United States Patent [19]

Immel et al.

[11] 4,247,485
[45] Jan. 27, 1981

[54] PROCESS FOR THE PREPARATION OF 2,2-DIMETHYLOLALKANALS

[75] Inventors: Otto Immel; Hans-Helmut Schwarz; Hein Quast, all of Krefeld, Fed. Rep. of Germany

[73] Assignee: Bayer Aktiengesellschaft, Leverkusen, Fed. Rep. of Germany

[21] Appl. No.: 22,009

[22] Filed: Mar. 19, 1979

[30] Foreign Application Priority Data

Mar. 25, 1978 [DE] Fed. Rep. of Germany ....... 2813201

[51] Int. Cl.³ .............................................. C07C 47/19
[52] U.S. Cl. ..................................... 568/464; 568/497
[58] Field of Search ......................................... 260/602

[56] References Cited

U.S. PATENT DOCUMENTS

| 272,852 | 7/1943 | Walter et al. | 229/92.7 |
| 2,863,878 | 12/1958 | Lynn | 260/602 |
| 3,135,808 | 6/1964 | Robeson et al. | 260/602 |

FOREIGN PATENT DOCUMENTS

| 2105922 | 8/1972 | Fed. Rep. of Germany | 260/602 |
| 2507461 | 2/1976 | Fed. Rep. of Germany | 260/602 |

Primary Examiner—Werren B. Lone
Attorney, Agent, or Firm—Sprung, Felfe, Horn, Lynch & Kramer

[57] ABSTRACT

A process for the preparation of 2,2-dimethylolalkanals is disclosed wherein formaldehyde is reacted with an aldehyde of the formula $$RCH_2CHO \qquad (I)$$

wherein
R denotes a straight-chain or branched alkyl radical with up to 12 carbon atoms where the radical can be substituted by an alkyl or alkoxy group with 1 to 3 carbon atoms in each case wherein the molar ratio of aldehyde of formula I to formaldehyde is 1:8 to 20, the reaction being carried out at a temperature in the range of 5° to 100° C. in the presence of 0.01 to 0.5 mol (per mol of aldehyde of formula (I)) of a catalyst consisting essentially of a hydroxide or carbonate of an alkali metal or alkaline earth metal or an unbranched tertiary aliphatic amine.

11 Claims, No Drawings

PROCESS FOR THE PREPARATION OF 2,2-DIMETHYLOLALKANALS

The invention relates to a process for the preparation of 2,2-dimethylolalkanals by reacting formaldehyde with aldehydes in the presence of bases.

It is known from DE-OS (German Published Pat. No.) 2,507,461 (see comparison example 2) to prepare 2,2-dimethylol-butanal by reacting formaldehyde with n-butylaldehyde in a molar ratio of approximately 3:1 in the presence of triethylamine. The yield of pure dimethylolbutanal is however unsatisfactory.

Furthermore, it is known from DE-OS (German Published Pat. No. 2,507,461 to prepare 2,2-dimethylolalkanals by reacting aldehydes with formaldehyde in the presence of specific tertiary branched alkylamines. Owing to the presence of specific tertiary branched alkylamines during the reaction the yield of dimethylolalkanals is increases. This process does however have the disadvantage that the specific tertiary branched alkylamines added during the condensation are accessible only with difficulty, this making the process relatively uneconomical.

It has now been found that 2,2-dimethylolalkanals can be obtained in a simple manner and in a good yield by reacting aldehydes with formaldehyde in the presence of bases, when aldehydes of the formula $$RCH_2CHO \qquad (I)$$

in which

R denotes an optionally substituted aliphatic radical, are reacted with formaldehyde in a molar ratio from 1:8 to 1:20 at temperatures in the range from 5° to 100° C. and in the presence of 0.01 to 0.5 mol (per mol aldeyde of the formula (I)) of hydroxides and/or carbonates of alkali metals and/or alkaline earth metals, and/or unbranched tertiary amines.

Particularly contemplated aliphatic radicals R are optionally substituted, straight-chain or branched alkyl radicals with up to 12, in particular 1 to 6, carbon atoms. Particularly contemplated substituents on these radicals are groups which are inert under the reaction conditions, in particular alkyl groups or alkoxy groups with 1 to 3 carbon atoms in each case. Examples which may be mentioned of aldehydes of the formula (I) are: 3-ethyl-, 3-n-propyl-, 3-isopropyl-, 3-n-butyl-, 3-isobutyl-, 3-sec.-butyl- and 3-tert.-butyl-butanal and the corresponding -n-pentanals, -n-hexanals and -n-heptanals; 4-ethyl-, 4-n-propyl-, 4-isopropyl-, 4-n-butyl-, 4-isobutyl-, 4-sec.-butyl- and 4-tert.-butyl-pentanals, -n-hexanals and -n-heptanals- 5-ethyl, 5-n-propyl-, 5-isopropyl-, 5-n-butyl-, 5-isobutyl-, 5-sec.-butyl- and 5-tert.-butyl-n-hexanals and -n-heptanals; 3-methyl-hexanal and 3-methyl-heptanal; 4-metyl-pentanal, 4-methyl-heptanal, 5-methyl-hexanal and 5-methylheptanal; and 3,3,5,-trimethyl-n-pentyl-, 3,3-diethylpentyl-, 4,4-diethylpentyl-, 3,3-dimethyl-n-butyl, 3,3-dimethyl-n-pentyl-, 5,5-dimethylheptyl-, 3,3-diemthylheptyl-, 3,3,4-trimethylpentyl-, 3,4-dimethyl-heptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl-, 3-methyl-4-ethylhexyl-, 3,3,4-trimethylpentyl-, 3,4,4-trimethylpentyl-, 3,3,4-trimethylhexyl-, 3,4,4-trimethylhexyl- and 3,3,4,4-tetramethylpentyl-aldehyde. Propanal, n-butanal, n-pentanal, 3-methylbutanal, n-hexanal, 3-methylpentanal, n-heptanal, 4-methylhexanal and n-octanal are preferred.

The process according to the invention will be illustrated by the equation below, using butyraldehyde as an example.

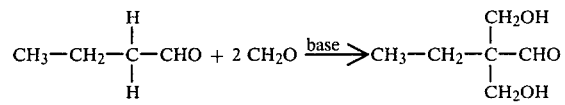

In the process according to the invention the aldehyde of the formula (I) can be reacted with formaldehyde in a molar ratio from about 1:8 to 1:20, particularly preferably in a molar ratio from 1:10 to 1:15, in the presence of 0.01 to 0.5 mol (per mol of aldehyde of formula (I)) of hydroxides and/or carbonates of alkali metals and/or alkaline earth metals, and/or unbranched tertiary amines, at temperatures in the range from about 5° to 100° C.

In general, formaldehyde is employed as an aqueous solution, preferably containing from 20 to 40% by weight of formaldehyde, and appropriately in a commercially available concentration.

Examples which may be mentioned of hydroxides and carbonates of alkali metals and alkaline earth metals are sodium hydroxide, potassium hydroxide, calcium hydroxide, barium hydroxide, sodium carbonate and potassium carbonate.

Suitable tertiary amines are heterocyclic, aliphatic and cycloaliphatic amines with up to 20 carbon atoms, preferably up to 15 carbon atoms, aliphatic tertiary amines preferably being employed. The tertiary amines which follow may be mentioned as examples: trimethylamine, tri-n-propylamine, triethylamine and tri-n-butylamine; and also unsymmetric trialkylamines, such as methyldipropylamine or dimethyl-butylamine; diamines, such as N,N-tetramethyl-ethylenediamine; N-N-dimethylcyclohexylamine; bis-(2-hydroxyethyl)-cyclohexylamine; N-methyl-pyrrolidine, N-methyl-piperidine and N-methyl-morpholine; and amines which are substituted by further functional groups, such as N,N-dimethylaminoethanol and bis-(2-hydroxy-ethyl)-cyclohexylamine. Further useful amines are also aliphatic amines, such as tribenzylamine and N,N-dimethylbenzylamine, and polyamines with tertiary amino groups, such as triethylenediamine and bis-(2-dimethylaminoethyl)-methylamine. Tetraalkylammonium hydroxides having alkylgroups with up to 4 carbon atoms, for example tetraethylammonium hydroxide, can also be employed as the base.

In the process according to the invention the hydroxides and/or carbonates of the alkali metals and/or alkaline earth metals and/or unbranched tertiary amines are preferably used in an amount from 0.05 to 0.1 mol, per mol of aldehyde of the formula (I); the pH value of the reaction solution is in general 8 to 13, preferably 9.5 to 12.5.

The amounts mentioned of hydroxides and/or carbonates of alkali metals and/or alkaline earth metals and/or unbranched tertiary amines are advantageous for the process according to the invention. These compounds can of course also be used in amounts above or below the above-mentioned range.

In carrying out the process according to the invention, it can be advantageous to add inert, organic solvents to the mixture of the aldehyde of the formula (I)

and the aqueous formaldehyde in order to achieve better solubility of the aldehyde of the formula (I) in the aqueous formaldehyde solution or to achieve a homogeneous solution.

Useful inert organic solvents are the solvents which are known for this, preferably lower aliphatic alcohols, such as methanol, ethanol, propanol and isopropanol, and aliphatic and alicyclic ethers, such as diethyl ether, tetrahydrofuran and dioxane.

The amount of solvent preferably used depends on the nature of the aldehyde of the formula (I) and can appropriately by determined by a few preliminary experiments.

The reaction temperatures for the process according to the invention are in general in the range from about 5° to 100° C., and are preferably 10° to 60° C. and particularly preferably 15° to 35° C.

The process according to the invention can be carried out either discontinuously or continuously. In the case of the discontinuous procedure, for example, aldehydes of the formula (I), the formaldehyde solution and the hydroxides and/or carbonates of the alkali metals and/or alkaline earth metals and/or unbranched tertiary amines, and if appropriate the organic solvent, can be brought together in the chosen ratio at the chosen temperature, with stirring and the reaction mixture can be kept at the reaction temperature for an appropriate time.

In general the reaction times are between 0.2 and 24 hours, in particular from 1 to 10 hours. The reaction time necessary in an individual case can easily be determined in the customary manner by following the course of the reaction using analytical methods or by a few preliminary experiments.

In general, the process according to the invention is carried out under normal pressure. However, one can also carry it out under reduced or increased pressure.

According to the process according to the invention the 2,2-dimethylolalkanals can surprisingly be obtained in high yields by using simple and easily accessible condensation agents. This makes the process a particularly economical preliminary stage to the industrial preparation of, for example, trimethylolpropane or trimethylolethane.

The trimethylolalkanes, for example trimethylolethane and trimethylolpropane, which can be prepared from 2,2-dimethylolaklanal by means of reduction, are intermediate products of industrial importance for the preparation of plasticizers, lacquer raw materials, polyesters and polyurethanes. 2,2-Dimethylolalkanals are also required for the preparation of dimethylolcarboxylic acids, for dyestuffs and agents for combating pests (Ullmann's Enzyklopädie der technischen Chemie (Ullmann's Encyclopaedia of industrial Chemistry), volume 3, pages 295 to 298).

The process according to the invention will be illustrated with the aid of the Examples which follow, but without being restricted to these Examples.

EXAMPLE 1

300 kg of an aqueous formaldehyde solution (about 30% by weight of formaldehyde, 3,000 mols) and 23.8 kg (330.6 mols) of n-butanal were introduced into a 500 l stirred kettle. 2.5 kg (25 mols) of triethylamine were added in the course of 2 hours, whilst stirring. The temperature was kept at 20 to 22° C. After 4 hours, the reaction mixture was analyzed. It contained 11.8% by weight of dimethylolbutyraldehyde, which corresponds to a yield of 88%, relative to the n-butanal employed.

EXAMPLE 2

50 kg of an aqueous formaldehyde solution (about 30% by weight of formaldehyde) and 3.6 kg (50 mols) of n-butanal are introduced into a stirred kettle and 250 g (3.4 mols) of Ca(OH)$_2$ are added. The reaction kettle was cooled. The temperature rose from 22° to 34° C. in the course of 20 minutes. After a total reaction time of 1 hour, the reaction had ended. Analysis of the reaction product gave, when converted, a yield of dimethylolbutanal of 88% of theory, relative to the n-butanal employed.

EXAMPLE 3

60 g (0.81 mol) of Ca(OH)$_2$ were added to 4,000 g of a 30% strength aqueous formaldehyde solution (40 mols). The mixture was stirred and cooled to 16° C. Thereafter, 144 g (2 mols) of n-butanal were added. The temperature thereby rose to 21° C. After a reaction time of about 1 hour, the reaction product was analyzed. It contained 5.7% of 2,2-dimethylolbutyraldehyde, which corresponds to a yield of 90.7%, relative to the n-butanal employed.

EXAMPLE 4

40 g of a 20% strength by weight sodium hydroxide solution (0.2 mol) were added dropwise to a mixture of 178 g (3 mols) of propanal and 3,000 g (30 mols) of a 30% strength aqueous formaldehyde solution in the course of 20 minutes, whilst stirring. The temperature thereby rose from 21° to 29° C. The reaction product was analyzed 1 hour after the addition of the sodium hydroxide solution. The product contained 10.3% of dimethylolpropanal, which corresponds to a yield of 93%, relative to the propanal employed.

EXAMPLE 5

72 g (1 mol) of butyraldehyde, 1,500 g of a 30% strength aqueous formaldehyde solution (15 mols) and 12 g (0.14 mol) of N-methylpyrrolidine were brought together and the mixture was kept at the boiling point for 40 minutes. Thereafter, 1,256 g of the reaction liquid were distilled off. 8 g (0.094 mol) of N-methylpyrrolidine were added to the distillate and the mixture was kept at the reflux temperature for half an hour. The product thus obtained was partly evaporated and the residue was combined with the residue of the first distillation. On the basis of an analysis, the mixture (714 g) contained 16.1% of 2,2-dimethylolbutanal, which corresponds to a yield of 87%, relative to the n-butanal employed.

EXAMPLE 6

72 g (1 mol) of n-butanal, 1,500 g of a 30% strength aqueous formaldehyde solution (15 mols) and 20 g (0.115 mol) of bis-(2-dimethylaminoethyl)-methylamine were kept at the boiling point for 20 minutes, using a reflux condenser. On the basis of an analysis, the reaction product contained 6.9% of dimethylolbutanal, which corresponds to a yield of 83%, relative to the n-butanal employed.

EXAMPLE 7

72 g (1 mol) of n-butanal, 1,000 g of a 30% strength aqueous formaldehyde solution (10 mols) and 50 g of an aqueous K$_2$CO$_3$ solution (0.05 mol) were combined and the mixture was stirred, whereupon the temperature rose to 41° C. and gradually fell again to room temperature. After 24 hours, the reaction product was analyzed. It contained 9.9% of dimethylolbutanal, which corresponds to a yield of 84%, relative to the n-butanal employed.

EXAMPLE 8

216 g (3 mols) of n-butanal, 3,000 g of a 30% strength aqueous formaldehyde solution (30 mols) and 30 g (0.3 mol) of triethylamine were brought together and the mixture was kept at the boiling point for 20 minutes. Thereafter, the reaction liquid was subjected to incipient distillation, 2,169 g of distillate being separated off. 10 g (0.1 mol) of triethylamine were added to the distillate and the mixture was kept at the reflux temperature for half an hour. This product was then distilled under normal pressure using a 30 cm packed column. The distillation residue (475 g) was combined with the residue of the first distillation. On the basis of an analysis, the mixture (1,545 g) contained 22.8% of dimethylolbutanal, which corresponds to a yield of 89%, relative to the n-butanal employed.

EXAMPLE 9

4,000 g of an aqueous formaldehyde solution (about 30% by weight of formaldehyde) (40 mols), 29.3 g (0.4 mol) of Ca(OH)$_2$ and 60.3 ml of a 40% aqueous trimethylamine solution (0.4 mol) were brought together and the mixture was stirred for 15 minutes. 292 (4 mols) of n-butanal were then added. The temperature thereby rose briefly from 25° to 36° C. and then fell again to 26° C. After a reaction time of 2 hours, the reaction mixture contained, on the basis of an analysis, 10.8% of 2,2-dimethylolbutanal, which corresponds to a yield of 89.6%, relative to the n-butanal employed.

EXAMPLE 10

60 g (0.81 mol) of Ca(OH)$_2$ were added to 4,000 g of a 30% strength aqueous formaldehyde solution (40 mols) and the mixture was stirred for 15 minutes, before 432 g (6 mols) of n-butanal were added. The temperature was kept between 10° and 15° C. by cooling the reaction vessel. After a reaction time of 3 hours, the reaction mixture contained, on the basis of an analysis, 14.8% of 2,2-dimethylolbutyraldehyde, which corresponds to a yield of 84%, relative to the n-butanal employed.

EXAMPLE 11

1.05 kg (14 mols) of Ca(OH)$_2$ were stirred into a mixture of 22.4 kg (31.1 mols) of n-butanal and 387.6 kg of a 30% strength aqueous formaldehyde solution (387.6 mols). The reaction kettle was cooled and was kept at 20°-24° C. After a reaction time of 5 hours, the reaction mixture contained, on the basis of an analysis, 8.7% of 2,2-dimethylolbutanal, which corresponds to a yield of 87%, relative to the n-butanal employed.

EXAMPLE 12

12 g of Ca(OH)$_2$ and 72 g of a 20% strength sodium hydroxide solution were added to 4,000 g of a 30% strength aqueous formaldehyde solution (40 mols). After a stirring time of 15 minutes, 288 g (4 mols) of n-butanal were added. The temperature in the reaction vessel thereby rose from 21° to 35° C. The reaction temperature was kept at 32° to 35° C. by external cooling. After a reaction time of 1 hour, the reaction mixture contained, on the basis of an analysis, 10.8% of 2,2-dimethylolbutanal, which corresponds to a yield of 88%, relative to the n-butanal employed.

What is claimed is:

1. A process for the preparation of 2,2-dimethylolalkanal which consists essentially of contacting formaldehyde with an aldehyde of the formula $$RCH_2CHO \tag{I}$$

wherein

R denotes a straight-chain or branched alkyl radical with up to 12 carbon atoms where the radical can be substituted by an alkyl or alkoxy group with 1 to 3 carbon atoms in each case, employing a molar ratio of formaldehyde to aldehyde of the formula (I) of 8–20:1 by carrying out the reaction at a temperature in the range of 5° to 100° C. in the presence of 0.01 to 0.5 mols (per mol of aldehyde of formula (I)) of a catalyst consisting essentially of a hydroxide or carbonate of an alkali metal or alkaline earth metal or an unbranched tertiary aliphatic amine or a tetraalkylammonium hydroxide.

2. A process according to claim 1 wherein the aldehyde of formula I is propionaldehyde.

3. A process according to claim 1 wherein the aldehyde of formula I is butyraldehyde.

4. A process according to claim 1 wherein the reaction of the aldehyde of formula I with formaldehyde is carried out at a pH of the reaction solution in the range of 8 to 13.

5. A process according to claim 4 wherein the pH range is 9.5 to 12.5.

6. A process according to claim 2 wherein the reaction is carried out in the presence of an alkali metal or alkaline earth metal hydroxide or carbonate and said alkali metal or alkaline earth metal hydroxide or carbonate is sodium hydroxide, potassium hydroxide, calcium hydroxide, barium hydroxide, sodium carbonate or potassium carbonate.

7. A process according to claim 1 wherein the reaction is carried out in the presence of an unbranched tertiary amine and said unbranched tertiary amine is a heterocyclic, aliphatic or cycloaliphatic amine with up to 20 carbon atoms.

8. A process according to claim 7 wherein said unbranched tertiary amine is trimethylamine, tri-n-propylamine, triethylamine, tri-n-butylamine, methyldipropylamine, dimethylbutylamine, N,N-tetramethylethylene diamine, N,N-dimethyl-cyclohexylamine, bis-(2-hydroxy-ethyl)cyclohexylamine, N-methyl-pyrrolidine, N-methylpiperidine, N-methyl-morpholine N,N-dimethylaminoethanol, bis-(2-hydroxy-ethyl)-cyclohexyl-amine, tribenzylamine, N,N-dimethylbenzylamine, triethylenediamine or bis-(2-dimethylaminoethyl)-methylamine.

9. A process according to claim 1 wherein the reaction of formaldehyde with the aldehyde of formula I is carried out in the presence of an organic solvent in which said aldehydes are soluble.

10. A process according to claim 9 wherein said organic solvent is a lower aliphatic alcohol, or aliphatic or alicyclic ether.

11. A process according to claim 9 wherein said solvent is methanol, ethanol, propanol, isopropanol and diethyl ether, tetrahydrofuran or dioxane.

* * * * *